United States Patent
Kang et al.

(10) Patent No.: US 9,174,926 B2
(45) Date of Patent: Nov. 3, 2015

(54) NORBORNENE-ESTER-BASED DERIVATIVE, METHOD FOR PREPARING SAME, AND USES THEREOF

(71) Applicants: Sangmyung University Seoul Industry-Academy Cooperation Foundation, Seoul (KR); Korea Research Institute of Chemical Technology, Daejeon (KR)

(72) Inventors: Ju Hui Kang, Gyeongsangnam-do (KR); Je Wan Woo, Seoul (KR); Yong Sung Park, Seoul (KR); Hyun Chul Oh, Seoul (KR); Jun Seong Park, Incheon (KR); Yi Wen Jin, Seoul (KR); Dae Hee Yun, Seoul (KR); Sang Jin Ko, Jeollabuk-do (KR); Kun Wu Chung, Chungcheongnam-do (KR); Yeong Un Kim, Daejeon (KR); Nam Kyun Kim, Daejeon (KR)

(73) Assignees: Sangmyung University Seoul Industry-Academic Cooperation Foundation, Seoul (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/616,454

(22) Filed: Feb. 6, 2015

(65) Prior Publication Data

US 2015/0152039 A1 Jun. 4, 2015

Related U.S. Application Data

(62) Division of application No. 14/005,772, filed as application No. PCT/KR2012/002082 on Mar. 22, 2012.

(30) Foreign Application Priority Data

Mar. 25, 2011 (KR) ........................ 10-2011-0027138

(51) Int. Cl.
*C07C 69/753* (2006.01)
*C07K 5/12* (2006.01)
*C07C 67/347* (2006.01)
*C08K 5/12* (2006.01)

(52) U.S. Cl.
CPC ............. *C07C 69/753* (2013.01); *C07C 67/347* (2013.01); *C08K 5/12* (2013.01); *C07C 2102/42* (2013.01)

(58) Field of Classification Search
None
See application file for complete search history.

(56) References Cited

PUBLICATIONS

Ishihara et al. Synlett, 1998, 10, 1053-1056.*
Du et al. "Asymmetric catalysis of Diels Alder Reaction" Handbook of cyclization reactions, vol. 1, 2010, pp. 1-57.*

* cited by examiner

*Primary Examiner* — Yevegeny Valenrod
(74) *Attorney, Agent, or Firm* — Abelman, Frayne & Schwab

(57) ABSTRACT

The present invention relates to norbornene-ester-based derivatives, to a method for preparing same, and to the uses thereof. This compound may be used as a plasticizer which can replace a phthalate-based plasticizer.

7 Claims, No Drawings

NORBORNENE-ESTER-BASED DERIVATIVE, METHOD FOR PREPARING SAME, AND USES THEREOF

RELATED APPLICATIONS

This application is a divisional application of co-pending U.S. patent application Ser. No. 14/005,772, which is United States national phase application under 35 USC §371 of PCT/KR2012/002082 filed on Mar. 22, 2012, and claims the benefit under 35 USC §119 of Korean patent application number KR 10-2011-0027138 filed Mar. 25, 2011, the disclosures of which are all incorporated herein by reference in their entireties.

TECHNICAL FIELD

The present invention relates to norbornene-ester-based derivatives, a method of preparing the same, and uses thereof.

BACKGROUND ART

Norbornene, which is a bridged six-membered carbon ring with a double bond at one side thereof, exhibits high reactivity because of the double bond and may thus be applied not only to optical materials, such as optical fibers, CD-ROMs and optical lenses but also to modified polymer materials, etc., and is thereby regarded as highly useful. In particular, polynorbornene known as a shape memory polymer resulting from polymerizing norbornene is efficiently utilized in medical machines, vehicle parts and living goods.

Meanwhile, a plasticizer added to products is a liquid or solid material which decreases the melting temperature and melting viscosity of rubber and plastics to increase processability and flexibility. A good plasticizer has low volatility, stability in heat and cold, flexibility at low temperature, high miscibility with rubber and plastics, and low efflux. In addition, a plasticizer is used to improve functions including electrical insulation properties, adhesion, cold resistance, etc. Currently, a plasticizer is mainly added to synthetic resin.

A phthalate-based plasticizer, including dioctyl phthalate (DOP), dibutyl phthalate (DBP), butylbenzyl phthalate (BBP), diisononyl phthalate (DINP), polyethyleneterephthalate (PET), etc., an adipate-based plasticizer, including dioctyl adipate (DOA), diisononyl adipate (DINA), etc., a fatty acid-based plasticizer, a phosphoric acid-based plasticizer, and a polyester-based plasticizer have been used. Particularly useful as the plasticizer is DOP which constitutes 72% of domestic plasticizer production.

DOP which started to be used in the 1930s is synthesized from phthalic acid and 2-ethylhexyl alcohol, and is very effective at increasing the processability of polyvinyl chloride resin. However, three kinds of phthalate-based plasticizers, including DOP, DBP and BBP, are indicated as suspected endocrine disrupters. The phthalate-based plasticizer was proven to have carcinogenicity, mutation-causing toxicity, and reproduction toxicity by the Scientific Committee on Toxicity, Ecotoxicity and the Environment of the EU, 2005, and thus the use thereof was banned.

In Korea, the phthalate-based plasticizer is classified as an environmental hormone material and thus the application thereof to all plastic toys and children's products has been banned from 2006. Because of the harmfulness of the phthalate-based plasticizer, the development of an eco-friendly plasticizer which can replace such a phthalate-based plasticizer is required.

DISCLOSURE

Technical Problem

As mentioned above, conventional phthalate-based plasticizers are obviously designated as endocrine disrupters, and restrictions thereof have been enhanced gradually by the EU. Therefore, culminating in the present invention, intensive and thorough research into solving the stability problems of the phthalate-based plasticizer encountered in the related art, resulted in the finding that an ester-based derivative having two norbornene groups obtained via a Diels-Alder reaction of cyclopentadiene and diacrylate may replace DOP, which is a typical example of a conventional phthalate-based plasticizer.

Accordingly, an object of the present invention is to provide norbornene-ester-based derivatives, which may replace phthalate-based plasticizers.

Another object of the present invention is to provide a method of preparing the norbornene-ester-based derivatives at high yield.

A further object of the present invention is to provide novel use of the norbornene-ester-based derivatives.

Technical Solution

In order to accomplish the above objects, the present invention provides norbornene-ester-based derivatives represented by Chemical Formula 1 below:

[Chemical Formula 1]

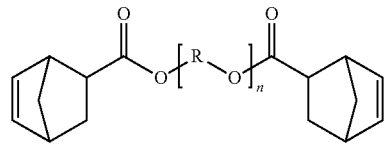

wherein R is linear or branched alkylene group having a carbon number of 1~20, and n is an integer of 1~15.

According to a preferred embodiment of the present invention, R is methylene, ethylene, n-propylene, iso-propylene, n-butylene, iso-butylene, tert-butylene, n-pentylene, iso-pentylene, tert-pentylene, n-hexylene, iso-hexylene, tert-hexylene, 2,3-dimethyl-hexylene, n-heptylene, iso-heptylene, n-octylene, iso-octylene, dimethyl octylene, n-nonylene, iso-nonylene, tert-nonylene, n-decylene, iso-decylene, tert-decylene, n-undecylene, iso-undecylene, tert-undecylene, n-dodecylene, iso-dodecylene, or tert-dodecylene.

According to a preferred embodiment of the present invention, R is ethylene, n-butylene, n-hexylene, iso-butylene, tert-pentylene, n-nonylene, or n-dodecyl.

According to a preferred embodiment of the present invention, when R is ethylene, n is 2 or 4.

According to a preferred embodiment of the present invention, when R is propylene, n is to 2 or 3.

In addition, the present invention provides a method of preparing the norbornene-ester-based derivatives represented by Chemical Formula 1 below, comprising subjecting diacrylate and cyclopentadiene to a Diels-Alder reaction at −20~100° C. using an organic solvent and a Lewis acid catalyst:

[Chemical Formula 1]

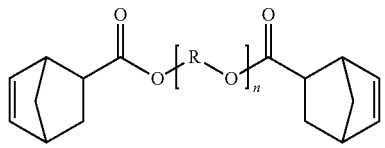

wherein R is linear or branched alkylene group having a carbon number of 1~20, and n is an integer of 1~15.

According to a preferred embodiment of the present invention, the organic solvent is chloroform, dichloromethane, carbon tetrachloride, dichloroethane, dibromoethane, dichloropropane, chlorobenzene, bromobenzene, ethylbenzene, benzene, toluene, para-xylene, n-pentane, n-octane, iso-octane, n-hexane, n-decane, n-dodecane, cyclohexane, cyclopentane, tetrahydrofuran, ethylacetate, methylacetate, nitroethane, acetone, methylethylketone, methylisobutylketone, cyclohexanone, iso-propylether, petroleum ether, butylether, ethylether, benzeneether, acetonitrile, propiononitrile, benzonitrile, dioxane, triethylamine, or dimethyl formamide, and is used in an amount of 50~500 parts by weight based on 100 parts by weight of the mixture of diacrylate and cyclopentadiene.

According to a preferred embodiment of the present invention, the Lewis acid catalyst is an aluminum-based material, a titanium-based material, tin, or zinc, and is used in an amount of 0.1~50 mol % based on the amount of the diacryalte.

According to a preferred embodiment of the present invention, the molar ratio of cyclopentadiene relative to 1 mol of the diacrylate is 1~6, and the reaction is performed for 1~10 hr.

According to a preferred embodiment of the present invention, the diacrylate is ethyleneglycol diacrylate, 1,6-hexanediol diacrylate, 1,4-butanediol diacrylate, nonanediol diacrylate, decanediol diacrylate, 1,3-butanediol diacrylate, di(ethylene glycol) diacrylate, tetra(ethylene glycol) diacrylate, 2,2-dimethyl-1,3-propanediol diacrylate, di(propylene glycol) diacrylate, tri(propylene glycol) diacrylate, or 1,6-hexanediol ethoxylate diacrylate.

In addition, the present invention provides a method of using the norbornene-ester-based derivatives represented by Chemical Formula 1 below as a plasticizer:

[Chemical Formula 1]

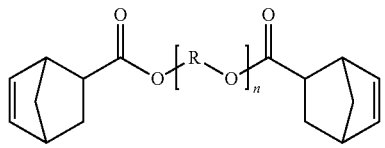

wherein R is linear or branched alkylene group having a carbon number of 1~20, and n is an integer of 1~15.

Advantageous Effects

According to the present invention, norbornene-ester-based derivatives can be used as plasticizers which will replace phthalate-based plasticizers toxic to humans, and the synthesis process thereof enables it to be prepared at high yield at room temperature and at normal pressure. Furthermore, these derivatives can be utilized as eco-friendly plasticizers which will replace conventional phthalate-based plasticizers, in fields of not only synthetic rubber, including isoprene rubber, styrene butadiene rubber, polychloroprene rubber, nitrile rubber, etc., but also a variety of plastics.

Mode for Invention

Hereinafter, a detailed description will be given of the present invention.

According to the present invention, norbornene-ester-based derivatives represented by Chemical Formula 1 below have two norbornene groups.

[Chemical Formula 1]

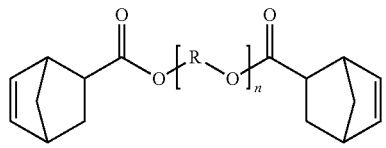

In the above chemical formula, R is linear or branched alkylene group having a carbon number of 1~20, and n is an integer of 1~15.

In Chemical Formula 1, R is of various alkylene groups and is saturated aliphatic. According to the present invention, R of Chemical Formula 1 is preferably a C1~12 linear or branched alkylene group, and specific examples thereof may include methylene, ethylene, n-propylene, iso-propylene, n-butylene, iso-butylene, tert-butylene, n-pentylene, iso-pentylene, tert-pentylene, n-hexylene, iso-hexylene, tert-hexylene, 2,3-dimethyl-hexylene, n-heptylene, iso-heptylene, n-octylene, iso-octylene, dimethyl octylene, n-nonylene, iso-nonylene, tert-nonylene, n-decylene, iso-decylene, tert-decylene, n-undecylene, iso-undecylene, tert-undecylene, n-dodecylene, iso-dodecylene, or tert-dodecylene. More preferably, ethylene, n-butylene, n-hexylene, iso-butylene, tert-pentylene, n-nonylene, or n-dodecyl is used.

Also, in Chemical Formula 1, [R—O] is a repeating unit group. If the repeating unit group becomes too long in proportion to an increase in n, the molecular weight of the resulting compound may become too large, making it difficult to expect desired properties. Hence, the value of n is preferably set to 1~10. Meanwhile, a compound in which n is 2 or 4 when R is ethylene, and a compound in which n is 2 or 3 when R is propylene are more preferably used as a plasticizer.

According to the present invention, the norbornene-ester-based derivatives represented by Chemical Formula 1 which may replace the conventional plasticizers are prepared via a Diels-Alder reaction of cyclopentadiene and any diacrylate.

When preparing the norbornene-ester-based derivatives according to the present invention, the molar ratio of cyclopentadiene relative to 1 mol of the diacryalte as the starting material is 1~6, preferably 3~4, and more preferably 4.

Examples of the preferred diacrylate of the present invention may include ethyleneglycol diacrylate, 1,6-hexanediol diacrylate, 1,4-butanediol diacrylate, nonanediol diacrylate, decanediol diacrylate, 1,3-butanediol diacrylate, di(ethylene glycol) diacrylate, tetra(ethylene glycol) diacrylate, 2,2-dimethyl-1,3-propanediol diacrylate, di(propylene glycol) diacrylate, tri(propylene glycol) diacrylate, or 1,6-hexanediol ethoxylate diacrylate.

Typically, a Diels-Alder reaction is mainly carried out at high temperature, and is thus problematic because the amount of byproducts is increased. In the present invention, the reaction is carried out at −20~100° C., and preferably 0~40° C., in order to prevent the production of byproducts and mitigate the reaction conditions. The reaction pressure is preferably set to the range of pressurized pressure to normal pressure, and more preferably normal pressure.

The reaction is performed in the presence of an organic solvent and a Lewis acid catalyst, and the usable catalyst may be a Lewis acid catalyst, including an aluminum-based material, a titanium-based material, tin, or zinc, and preferably aluminum chloride is used. The catalyst may be used in an amount of 0.1~50 mol %, and preferably 5~10 mol %, based on the amount of the diacrylate. Examples of the usable organic solvent may include chloroform, dichloromethane, carbon tetrachloride, dichloroethane, dibromoethane, dichloropropane, chlorobenzene, bromobenzene, ethylbenzene, benzene, toluene, para-xylene, n-pentane, n-octane, iso-octane, n-hexane, n-decane, n-dodecane, cyclohexane, cyclopentane, tetrahydrofuran, ethylacetate, methylacetate, nitroethane, acetone, methylethylketone, methylisobutylketone, cyclohexanone, iso-propylether, petroleum ether, butylether, ethylether, benzeneether, acetonitrile, propiononitrile, benzonitrile, dioxane, triethylamine, or dimethyl formamide, and the organic solvent may be used in an amount of 50~500 parts by weight based on 100 parts by weight of the mixture of diacrylate and cyclopentadiene. The reaction time is set to 1~10 hr after addition of reactants, and is preferably 1~2 hr after instillation.

In order to remove the remaining solvent and cyclopentadiene, evaporation is performed under reduced pressure. When the reaction product is dewatered and dried using magnesium sulfate, the norbornene-ester-based derivatives represented by Chemical Formula 1 may be obtained.

Meanwhile, the norbornene-ester-based derivatives according to the present invention may replace the conventional phthalate-based plasticizers. In the present invention, usability as an eco-friendly plasticizer was ascertained via a rubber composition containing the above compound. Also, the derivatives of the invention may be used as eco-friendly plasticizers which will replace the conventional phthalate-based plasticizers, in fields of not only synthetic rubber, such as isoprene rubber, styrene butadiene rubber, polychloroprene rubber, and nitrile rubber, but also various plastics.

Below is a more detailed description of the present invention through the following examples and comparative examples, which are not construed to limit the present invention.

Example 1

The reaction was carried out for 2 hr using 500 ml of dichloromethane ($CH_2Cl_2$), 0.04 mol (5.331 g, use of 10 mol % based on the amount of diacrylate) of aluminum chloride ($AlCl_3$), 0.40 mol (90.5 g) of 1,6-hexanediol diacrylate, and 1.6 mol (105.8 g) of cyclopentadiene. The reaction product was washed with brine and dewatered. In order to remove the solvent and the byproduct, that is, dicyclopentadiene, washing filtration was performed using methanol and hexane. The resulting product was dried in vacuum for about 12 hr or more, yielding 0.377 mol (135 g) of 1,6-hexanediol di(5-norbornene-2-carboxylate) as the norbornene-ester-based derivative represented by Chemical Formula 1. NMR of this compound is as follows.

$^1$H-NMR δ(ppm): 5.87-6.15(4H, m), 3.99(4H, m), 2.86-3.16(6H, m), 1.33-1.64(16H, m)

Example 2

This example was performed in the same manner as in Example 1, with the exception that 0.30 mol (59.5 g) of 1,3-butanediol diacrylate was used instead of 1,6-hexanediol diacrylate of Example 1, cyclopentadiene was used in an amount of 1.2 mol (79.3 g) corresponding to four times the mol number of the diacrylate, and aluminum chloride ($AlCl_3$) was used in an amount of 0.03 mol (4.00 g) corresponding to 10 mol % based on the amount of the diacrylate. Finally, 0.26 mol (85.9 g) of 1,3-butanediol di(5-norbornene-2-carboxylate) was obtained as the norbornene-ester-based plasticizer of Chemical Formula 1. NMR of this compound is as follows.

$^1$H-NMR δ(ppm): 5.89-6.16(4H, m), 4.92(1H, m), 3.16, 2.98, 2.86(6H, m), 1.19-1.88(13H, m)

Example 3

This example was performed in the same manner as in Example 1, with the exception that 0.30 mol (64.3 g) of di(ethylene glycol) diacrylate was used instead of 1,6-hexanediol diacrylate of Example 1, cyclopentadiene was used in an amount of 1.2 mol (79.3 g) corresponding to four times the mol number of the diacrylate, and aluminum chloride ($AlCl_3$) was used in an amount of 0.03 mol (4.00 g) corresponding to 10 mol % based on the amount of the diacrylate. Finally, 0.24 mol (83.1 g) of di(ethylene glycol) di(5-norbornene-2-carboxylate) was obtained as the norbornene-ester-based plasticizer of Chemical Formula 1. NMR of this compound is as follows.

$^1$H-NMR δ(ppm): 5.91-6.15(4H, m), 4.13(4H, m), 3.66 (4H, m), 3.18, 3.00, 2.87(6H, m), 1.27-1.41(8H, m)

Example 4

This example was performed in the same manner as in Example 1, with the exception that 0.30 mol (91.0 g) of tetra(ethylene glycol) diacrylate was used instead of 1,6-hexanediol diacrylate of Example 1, cyclopentadiene was used in an amount of 1.2 mol (79.3 g) corresponding to four times the mol number of the diacrylate, and aluminum chloride ($AlCl_3$) was used in an amount of 0.03 mol (4.00 g) corresponding to 10 mol % based on the amount of the diacrylate. Finally, 0.274 mol (118.8 g) of tetra(ethylene glycol) di(5-norbornene-2-carboxylate) was obtained as the norbornene-ester-based plasticizer of Chemical Formula 1. NMR of this compound is as follows.

$^1$H-NMR δ(ppm): 5.19-6.15(4H, m), 4.13(4H, m), 3.60 (12H, m), 3.29, 3.17, 2.86(6H, m), 1.32-1.88(8H, m)

Example 5

This example was performed in the same manner as in Example 1, with the exception that titanium chloride ($TiCl_4$) was used in the same mol number, instead of aluminum chloride ($AlCl_3$) of Example 1. Finally, the derivative of this example was the same as the derivative of Example 1 and was obtained in an amount of 0.31 mol (111 g).

Example 6

This example was performed in the same manner as in Example 2, with the exception that titanium chloride ($TiCl_4$) was used in the same mol number, instead of aluminum chloride ($AlCl_3$) of Example 2. Finally, the derivative of this example was the same as the derivative of Example 2 and was obtained in an amount of 0.24 mol (79.3 g).

Example 7

This example was performed in the same manner as in Example 3, with the exception that titanium chloride ($TiCl_4$) was used in the same mol number, instead of aluminum chloride ($AlCl_3$) of Example 3. Finally, the derivative of this example was the same as the derivative of Example 3 and was obtained in an amount of 0.23 mol (79.6 g).

Example 8

This example was performed in the same manner as in Example 4, with the exception that titanium chloride ($TiCl_4$) was used in the same mol number, instead of aluminum chloride ($AlCl_3$) of Example 4. Finally, the derivative of this example was the same as the derivative of Example 4 and was obtained in an amount of 0.25 mol (108.4 g).

Comparative Examples 1 and 2

Based on 100 parts by weight of raw rubber in the composition shown in Table 1 below, a phthalate-based plasticizer was not added in Comparative Example 1, and 3 parts by weight of DOP as the phthalate-based plasticizer was added in Comparative Example 2.

Test Example

Examples 1 to 4 were reactions using the aluminum chloride catalyst, and Examples 5 to 8 were reactions using the titanium chloride catalyst. The derivatives of Examples 5 to 8 were the same as those of Examples 1 to 4 despite the use of different catalysts, and thus the properties of the plasticizer were tested using only Examples 1 to 4.

The test was conducted using the compositions of Table 1. The same raw rubber and mixing components were used except for the plasticizer, and the plasticizer was added in the same amount of 3 parts by weight based on 100 parts by weight of raw rubber.

In order to perform testing in a pure rubber state, the compositions were prepared without the use of a filler, and instead of TBBS as a vulcanization accelerator, CZ of the same sulfenamide type was used. As shown in Table 1, the mixing was performed in such a manner that raw rubber was subjected to mastication for about 5 min using an open roll, and then mixed with the other mixing components and kneaded for about 5 min.

The same raw rubber and mixing components were used except for the plasticizer, and the plasticizer was added in the same amount of 3 parts by weight based on 100 parts by weight of raw rubber. The resulting mixture was measured in terms of Mooney viscosity, scorch time and maximum torque value using a Mooney viscometer (Myungji Tech, 2007) and a rheometer (Myungji Tech, 2007) in order to evaluate processability. Mooney viscosity was measured at 100° C. for 4 min, and measurement was carried out at 150° C. for 60 min using a rheometer, and the results were recorded.

TABLE 1

|  | Comp. Ex. 1 | Comp. Ex. 2 | Ex. 1 | Ex. 2 | Ex. 3 | Ex. 4 |
| --- | --- | --- | --- | --- | --- | --- |
| Isoprene rubber | 100 | 100 | 100 | 100 | 100 | 100 |
| Zinc oxide | 5 | 5 | 5 | 5 | 5 | 5 |
| Sulfur | 2.25 | 2.25 | 2.25 | 2.25 | 2.25 | 2.25 |
| Stearic acid | 2 | 2 | 2 | 2 | 2 | 2 |
| CZ | 0.7 | 0.7 | 0.7 | 0.7 | 0.7 | 0.7 |
| DOP | — | 3 |  |  |  |  |
| Compound of Ex. 1 |  |  | 3 |  |  |  |
| Compound of Ex. 2 |  |  |  | 3 |  |  |
| Compound of Ex. 3 |  |  |  |  | 3 |  |
| Compound of Ex. 4 |  |  |  |  |  | 3 |
| Total (wt parts) | 109.95 |  |  | 112.95 |  |  |

Results of Measurement of Mooney Viscosity

Mooney viscosity refers to the viscosity of non-vulcanized rubber, and Mooney viscosity affects processability of rubber and properties of vulcanized rubber. The following Table 2 shows the results of measurement of Mooney viscosity. When DOP was added, there was little change in Mooney viscosity compared to when the plasticizer was not added. However, when the same amount of the norbornene-ester-based plasticizer was added, Mooney viscosity was changed to 9.6~16.4 compared to when the plasticizer was not added. Changes in Mooney viscosity may vary depending on the compatibility with raw rubber or the molecular weight distribution. The norbornene-ester-based plasticizers used in this testing are regarded as having good compatibility with raw rubber (isoprene rubber).

TABLE 2

Results of measurement of Mooney viscosity

|  | Comp. Ex. 1 | Comp. Ex. 2 | Ex. 1 | Ex. 2 | Ex. 3 | Ex. 4 |
| --- | --- | --- | --- | --- | --- | --- |
| Mooney viscosity $ML_{1+4}(100)$ | 16.8 | 18.8 | 33.2 | 30.1 | 29.0 | 29.8 |

Results of Measurement Using Rheometer

A rheometer was used to measure vulcanization conditions of rubber, and scorch time (ts1) and the properties of vulcanized rubber could be estimated from rheometer curves. The following Table 3 shows the results of measurement using a rheometer. Scorch time indicates the early vulcanization time, and causes fluidity to deteriorate in the process, and is considered to be an important parameter for application to the process. Scorch time was represented in the sequence of Example 1>Example 2>Example4>Example 3>Comparative Example 2 when the plasticizer was added. This means that when the same amount of the plasticizer is added, the scorch time of the examples is longer than that of Comparative Example 2, thus facilitating the control of the process.

Also, the maximum torque (MH) able to estimate the properties was similar to that of Comparative Example 2, and t90 indicating the time at which 90% vulcanization begins to occur is longer in the examples than in Comparative Example 2.

TABLE 3

Results of measurement using rheometer (measurement conditions: at 150° C. for 60 min)

|  | Minimum Torque (ML) [lb-in] | Maximum Torque (MH) [lb-in] | Scorch Time (ts1) [min] | tc90 [min] |
| --- | --- | --- | --- | --- |
| Comp. Ex. 1 | 1.47 | 19.08 | 7.20 | 15.78 |
| Comp. Ex. 2 | 1.57 | 17.49 | 7.40 | 15.68 |
| Ex. 1 | 3.31 | 17.56 | 8.70 | 19.27 |
| Ex. 2 | 3.14 | 17.15 | 8.60 | 18.01 |
| Ex. 3 | 2.80 | 17.20 | 7.30 | 16.59 |
| Ex. 4 | 2.99 | 17.77 | 7.38 | 16.68 |

As is apparent from Tables 2 and 3, the norbornene-ester-based derivative prepared via a Diels-Alder reaction of cyclopentadiene and diacrylate was evaluated to have properties equal to or greater than those of conventional DOP to the extent that it could replace DOP as the plasticizer.

The present invention provides novel norbornene-ester-based derivatives, which can replace DOP which is a conventional phthalate-based plasticizer harmful to humans. More particularly, the plasticizer can be prepared via a Diels-Alder reaction of cyclopentadiene and to any diacrylate, and as a result of evaluating the properties of the mixture resulting from mixing rubber with the norbornene-ester-based plasticizer of the present invention, the derivatives of the present invention can replace DOP as the conventional phthalate-based plasticizer, and can also be applied as plasticizers for plastics.

The invention claimed is:

1. A method of preparing norbornene-ester-based derivatives represented by Chemical Formula 1 below, comprising subjecting diacrylate and cyclopentadiene to a Diels-Alder reaction at −20~100° C. using an organic solvent and a Lewis acid catalyst:

[Chemical Formula 1]

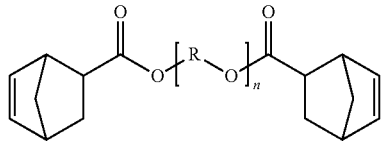

wherein R is ethylene or propylene, and when R is ethylene n is 2 or 4, and when R is propylene n is 2 or 3.

2. The method of claim 1, wherein the organic solvent is chloroform, dichloromethane, carbon tetrachloride, dichloroethane, dibromoethane, dichloropropane, chlorobenzene, bromobenzene, ethylbenzene, benzene, toluene, para-xylene, n-pentane, n-octane, iso-octane, n-hexane, n-decane, n-dodecane, cyclohexane, cyclopentane, tetrahydrofuran, ethylacetate, methylacetate, nitroethane, acetone, methylethylketone, methylisobutylketone, cyclohexanone, iso-propylether, petroleum ether, butylether, ethylether, benzeneether, acetonitrile, propiononitrile, benzonitrile, dioxane, triethylamine, or dimethyl formamide, and is used in an amount of 50~500 parts by weight based on 100 parts by weight of a mixture of the diacrylate and the cyclopentadiene.

3. The method of claim 1, wherein the Lewis acid catalyst is an aluminum-based material, a titanium-based material, tin, or zinc, and is used in an amount of 0.1~50 mol % based on an amount of the diacryalte.

4. The method of claim 1, wherein a molar ratio of the cyclopentadiene relative to 1 mol of the diacrylate is 1~6, and the reaction is performed for 1~10 hr.

5. The method of claim 1, wherein the diacrylate is ethyleneglycol diacrylate, 1,6-hexanediol diacrylate, 1,4-butanediol diacrylate, nonanediol diacrylate, decanediol diacrylate, 1,3-butanediol diacrylate, di(ethylene glycol) diacrylate, tetra(ethylene glycol) diacrylate, 2,2-dimethyl-1,3-propanediol diacrylate, di(propylene glycol) diacrylate, tri(propylene glycol) diacrylate, or 1,6-hexanediol ethoxylate diacrylate.

6. The method of claim 1, further comprising using norbornene-ester-based derivatives represented by chemical formula 1 as a plasticizer.

7. The method of claim 6, wherein the plasticizer is added to rubber or plastic.

* * * * *